United States Patent [19]

Hayashi et al.

[11] Patent Number: 5,446,167
[45] Date of Patent: Aug. 29, 1995

[54] PROCESS FOR SEPARATING ISOMERS OF AZOLYLMETHYLCYCLOPENTANOL DERIVATIVES

[75] Inventors: Shoichiro Hayashi; Kazuhiko Sunagawa; Satoru Kumazawa, all of Iwaki, Japan

[73] Assignee: Kureha Kagaku Kogyo Kabushiki Kaisha, Tokyo, Japan

[21] Appl. No.: 321,093

[22] Filed: Oct. 11, 1994

[30] Foreign Application Priority Data

Oct. 13, 1993 [JP] Japan .................................. 5-280103

[51] Int. Cl.$^6$ .................. C07D 249/08; C07D 233/60
[52] U.S. Cl. ............................... 548/262.2; 548/335.1
[58] Field of Search .................. 548/335.1, 262.2; 514/396, 383

[56] References Cited

U.S. PATENT DOCUMENTS

| | | | |
|---|---|---|---|
| 4,938,792 | 7/1990 | Kamazawa et al. | 71/92 |
| 5,142,061 | 8/1992 | Briner | 548/267.8 |
| 5,225,430 | 7/1993 | Minoguchi et al. | 514/383 |

FOREIGN PATENT DOCUMENTS

| | | |
|---|---|---|
| 0267778A2 | 5/1988 | European Pat. Off. |
| 0324646A2 | 7/1989 | European Pat. Off. |
| 0329397 | 8/1989 | European Pat. Off. |
| 0341954A1 | 11/1989 | European Pat. Off. |
| 0357404A3 | 4/1990 | European Pat. Off. |
| 0488348A1 | 6/1992 | European Pat. Off. |
| 0488395A1 | 6/1992 | European Pat. Off. |
| 0488396A2 | 6/1992 | European Pat. Off. |

OTHER PUBLICATIONS

S. Oae, "Datsuri Hannou, Koza Yuki Hannou Kiko 6 (Elimination Reaction, Mechanism's Lecture vol. 6) (M. Imoto, ed.)", pp. 164–165, Tokyo Kagaku Dojin, Tokyo, 1965.

The Chemistry of the Hydroxyl Group, Part 2, Edited by Saul Patai.

Primary Examiner—Robert W. Ramsuer
Assistant Examiner—Laura Cross
Attorney, Agent, or Firm—McAulay Fisher Nissen Goldberg & Kiel

[57] ABSTRACT

A process for separating a cis isomer from a mixture of the cis isomer and a trans isomer of an azolylmethylcyclopentanol derivative of the formula (I):

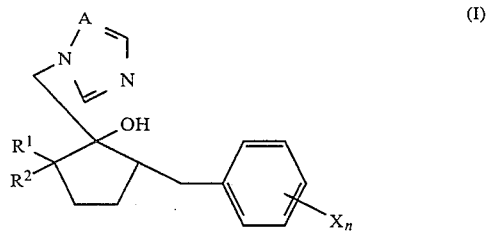

wherein, $R^1$ and $R^2$ each independently represent a hydrogen atom or an alkyl group; each X represents a halogen atom, an alkyl group, a haloalkyl group, a phenyl group, a cyano group or a nitro group; n is an integer of from 0 to 5; A represents a nitrogen atom or a CH group; and each X may be identical or different when n is an integer of from 2 to 5, comprising the steps of dehydrating selectively the trans isomer in the presence of an acid and isolating the cis isomer.

4 Claims, No Drawings

PROCESS FOR SEPARATING ISOMERS OF AZOLYLMETHYLCYCLOPENTANOL DERIVATIVES

BACKGROUND OF THE INVENTION

The present invention relates to a process for separating geometric isomers of azolylmethylcyclopentanol derivatives having fungicidal activity. Fungicidally active azolylmethylcyclopentanol derivatives represented by the formula (I):
wherein, $R^1$ and $R^2$ each independently represent a hydrogen atom or an alkyl group; each X represents a halogen atom, an alkyl group, a haloalkyl group, a phenyl group, a cyano group or a nitro group; n is an integer of from 0 to 5; A represents a nitrogen atom or a CH group; and each X may be identical or different when n is an integer of from 2 to 5, exist in two stereoisomeric forms, one of which is a geometric isomer having a hydroxy group and a benzyl group on the same side about the plane of the cyclopentane ring (hereinafter referred to as cis isomer), and the other is a geometric isomer having a hydroxy group and a benzyl group on the opposite side about the plane of the cyclopentane ring (hereinafter referred to as trans isomer). Of these two kinds of isomers, the cis isomer is known to exhibit greater fungicidal activity.

The processes for obtaining the cis isomer, therefore, have been proposed as in the following:

(1) An oxirane derivative in cis form (isomer in which an oxygen atom in the oxirane ring and a benzyl group are placed on the same side about the plane of the cyclopentane ring) of the following formula (A) is separated by silica gel column chromatography, and the separated oxirane derivative in cis form is then converted into an azolylmethylcyclopentanol derivative of the following formula (A-I) (U.S. Pat. No. 4,938,792).

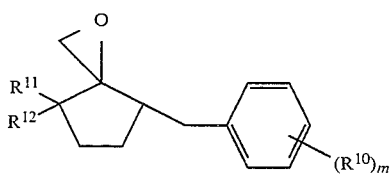

(A)

Azolation

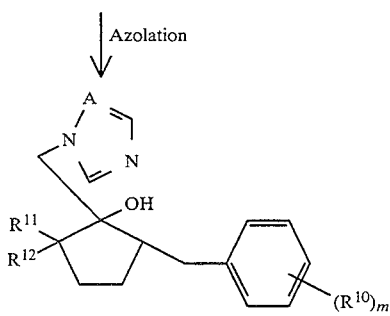

(A-I)

In the formulae above, $R^{11}$ and $R^{12}$ each independently represent a hydrogen atom or a $C_1$–$C_5$ alkyl group; $R^{10}$ represents a halogen atom, a $C_1$–$C_5$ alkyl group or a phenyl group; m is an integer of from 0 to 2; and A represents a nitrogen atom or a CH group; provided that both $R^{11}$ and $R^{12}$ do not represent a hydrogen atom simultaneously.

(2) A 1,2-diol derivative of the following formula (B) is converted into an azolylmethylcyclopentanol derivative in cis form of the following formula (B-1) (U.S. Pat. No. 5,142,061).

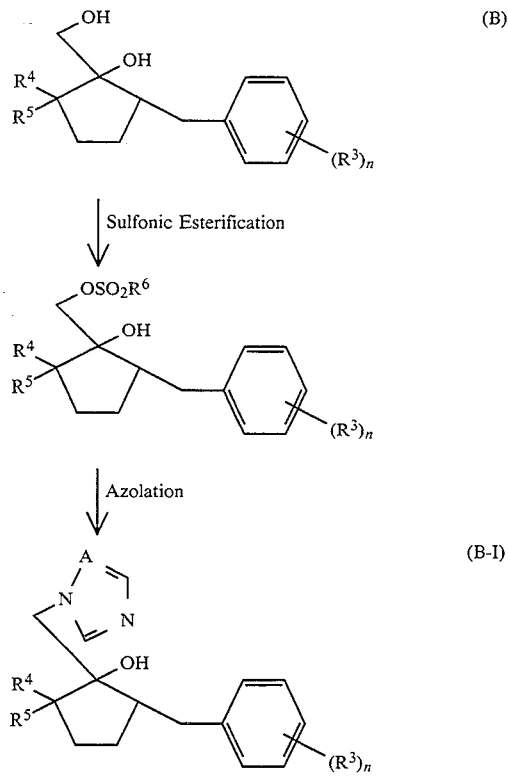

In the formulae above, n is an integer of from 0 to 5; $R^3$ represents a halogen atom, a nitro group, a cyano group, an alkyl group, a haloalkyl group or a phenyl group; $R^4$ and $R^5$ each independently represent a hydrogen atom or an alkyl group; A represents a nitrogen atom or a CH group; and $R^6$ represents an optionally substituted alkyl or aryl group.

(3) An azolylmethyloxabicyclohexane derivative of the following formula (C) is reduced into an azolylmethylcyclopentanol derivative in cis form of the following formula (C-1) (U.S. Pat. No. 5,225,430).

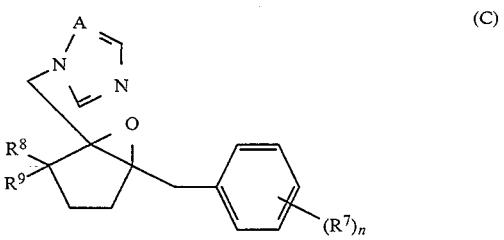

(C)

Reduction

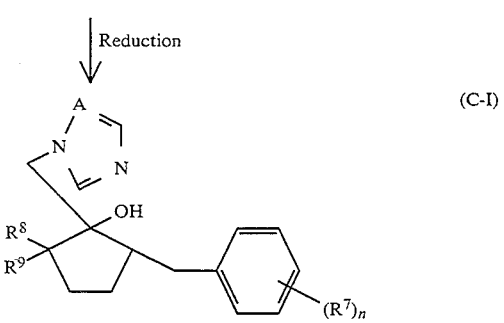

(C-I)

In the formulae above, $R^7$ represents a halogen atom, a nitro group, a cyano group, an alkyl group, a haloalkyl group or a phenyl group; $R^8$ and $R^9$ each independently represent a hydrogen atom or an alkyl group; n is an integer of from 0 to 5; and A represents a nitrogen atom or a CH group.

There have never been proposed, however, the processes for separating a cis isomer from a mixture of geometric isomers of the azolylmethylcyclopentanol derivative produced according to usual processes.

The present inventors, as a result of continuous and earnest studies, have found that a cis isomer of high purity can be separated from a geometric isomer mixture of the compound of the formula (I) by subjecting the mixture to dehydration under acidic condition. Based on the finding, the present invention has been achieved.

SUMMARY OF THE INVENTION

An object of the present invention is to provide a process for efficiently separating a cis isomer of an azolylmethylcyclopentanol derivative of the formula (I) which exhibits a high fungicidal activity.

In an aspect of the present invention, there is provided a process for separating a cis isomer from a mixture of the cis isomer and a trans isomer of an azolylmethylcyclopentanol derivative of the formula (I):
wherein, $R^1$ and $R^2$ each independently represent a hydrogen atom or an alkyl group; each X represents a halogen atom, an alkyl group, a haloalkyl group, a phenyl group, a cyano group or a nitro group; n is an integer of from 0 to 5; A represents a nitrogen atom or a CH group; and each X may be identical or different when n is an integer of from 2 to 5, comprising the steps of dehydrating selectively the trans isomer in the presence of an acid and isolating the cis isomer.

DETAILED DESCRIPTION OF THE INVENTION

In the structural formulae of the compounds set forth herein, each bond is shown by a full line irrespective of the attached side about the plane of the cyclopentane ring.

In the formula (I), $R^1$, $R^2$, X and n are preferably as follows:

$R^1$ and $R^2$ each independently represent a hydrogen atom or a $C_1$-$C_5$ alkyl group;

X represents a fluorine atom, a chlorine atom, a bromine atom, a $C_1$-$C_4$ alkyl group, a $C_1$-$C_4$ haloalkyl group, a phenyl group, a cyano group or a nitro group; and n is an integer from 0 to 2.

The haloalkyl group means a group in which one or more hydrogen atoms in the alkyl group are substituted with halogen atoms. An example of the haloalkyl group is a trifluoromethyl group.

It has been believed that trans-elimination is preferential during the dehydration of cycloalkanols in the presence of an acid catalyst. For example, it is described: "There is a report that during the dehydration of 2-alkylhexanols in the presence of an acid catalyst, cis isomers (H and OH therein are of the trans configuration) are much easily dehydrated than trans isomers (H and OH therein are of the cis configuration) to produce an olefin." [S. Oae, in "Datsuri Hannou, Koza Yuki Hannou Kiko 6 (Elimination Reaction, Organic Reaction Mechanism's Lecture Vol. 6) (M. Imoto, ed.)", pp.164–165, Tokyo Kagaku Dojin, Tokyo, 1965].

The present inventors, however, have surprisingly found that, in the case of the cyclopentane ring, trans-elimination is difficult during the dehydration reaction of a hydroxy group and a hydrogen atom bonded to the carbon atom which, in the cyclopentane ring, is adjacent to the carbon atom, to which the hydroxy group is bonded, in the presence of an acid catalyst, and have reached the separation process of the present invention.

Thus, it has been expected that, when a mixture of cis isomer and trans isomer of the compound of the formula (I) is dehydrated in the presence of an acid catalyst, the cis isomer is dehydrated prior to trans isomer. Contrary to such conventional expectation, in fact, the dehydration of cis isomer does not occur, and consequently the cis isomer of high purity has remained as an unreacted product.

Dehydration is generally conducted in the presence of a diluent (dispersing medium or solvent). Examples of the suitable diluent are set forth in the following:

Water; an organic acid such as formic acid, acetic acid and propionic acid; an aromatic hydrocarbon such as benzene, toluene and xylene; an aliphatic hydrocarbon such as petroleum ether, pentane, hexane, heptane, methylcyclohexane and ethylcyclohexane; a halogenated hydrocarbon such as methylene chloride, chloroform and carbon tetrachloride; an alcohol such as methanol, ethanol, i-propanol and t-butanol; an ether such as diethylether, dimethoxyethane, diisopropylether, tetrahydrofuran, diglyme and dioxane; carbon disulfide; acetonitrile; acetone; ethyl acetate; acetic anhydride; pyridine; dimethylformamide; dimethylacetamido; N-methyl-2-pyrrolidinone; dimethylsulfoxide; hexamethylphosphoramide; etc.

These diluents may be used alone or as a mixture of two or more.

Among these diluents, an aromatic hydrocarbon and an alcohol are preferably used.

Examples of the acid include: an inorganic acid such as hydrochloric acid, hydrobromic acid, hydroiodic acid, sulfuric acid, phosphoric acid and nitric acid; a carboxylic acid such as formic acid, acetic acid and butyric acid; an aromatic sulfonic acid such as p-toluene sulfonic acid; a strongly acidic cation exchange resin having a sulfo group. Preferably, sulfuric acid or p-toluenesulfonic acid is used. These acids may be used alone or as a mixture of two or more.

Acids can be used in a catalytically effective amount and usually are used in an amount of 0.1 to 10 in molar ratio to the mixture of cis isomer and trans isomer.

The process of the present invention is applicable to those compounds of formula (I) in which the cis isomer and the trans isomer are mixed in any proportions. The process can be applied, for example, to the compound produced by the process described in EP 329397 A, which process produces a mixture of cis and trans isomers.

In the presence of the acid as a catalyst, the mixture of cis isomer and trans isomer dissolved or dispersed in the diluents may be subjected to the selective dehydration reaction of trans isomer at a temperature near the refluxing point of the diluent for about several hours.

Although reaction conditions such as temperature and time may be suitably selected depending on the concentration of acid present in the reaction mixture and on whether or not azeotropic dehydration is adopted, a reaction temperature and a reaction time are usually from 50° to 100° C. and from 1 to 10 hours, respectively.

Dehydrated products are compounds resulting from the dehydration of a hydroxy group and a hydrogen atom bonded to the carbon atom which is adjacent to the carbon atom, to which the hydroxy group is bonded, as well as interchangeable isomers thereof. Thus, the cis isomer can be easily isolated from the reaction mixture through an ordinary purification process.

Recrystallization from organic solvents, washing with organic solvents, silica gel chromatography, sulfate purification method in which a salt is produced by the azole ring and sulfuric acid, the resultant salt is purified, then neutralized and isolated, and the like can be suitably applied. Preferably, the recrystallization or the washing method is used.

According to the present invention, by using dehydration in the presence of an acid catalyst, the cis isomer of high fungicidal activity can be effectively separated from the mixture of the cis isomer and the trans isomer of azolylmethylcyclopentanol derivative.

EXAMPLES

The present invention will now be described by way of examples which are to be considered by no means limitative without departing from the scope of the invention. Composition of isomers is analyzed by gas chromatography using a fused silica capillary column.

EXAMPLE 1

Separation of cis isomer of 5-(4-chlorobenzyl)-2,2-dimethyl-1-(1H-1,2,4-triazol-1-ylmethyl)cyclopentanol 20.0 g of a mixture of 81.0 wt % of cis isomer and 19.0 wt % of trans isomer of 5-(4-chlorobenzyl)-2,2-dimethyl-1-(1H-1,2,4-triazol-1-ylmethyl) cyclopentanol was dissolved in 300 ml of toluene, and after addition of 2.6 g of 95% sulfuric acid (molar ratio of sulfuric acid to isomer mixture=0.4/1.0) at 20° C., heated at reflux on oil bath, causing azeotropic dehydration with toluene.

After 5 hours, the reaction solution was cooled to room temperature, and after addition of 200 ml of 5% aqueous sodium hydroxide solution, stirred vigorously.

Then, the toluene layer, after washing 3 times with water, was dried over anhydrous sodium sulfate and toluene was distilled off under reduced pressure to obtain 19.7 g of solid.

The solid contained 80.7 wt % of cis isomer and 1.5 wt % of trans isomer. The yield of cis isomer at this stage was 98.1% and the decomposition ratio of trans isomer was 92.1%.

The solid obtained through the dehydration was dissolved in 160 ml of methylcyclohexane with heating, and then cooled to 0° C. at a rate of 10° C./60 min. The precipitated crystals were filtered off, and the filtered crystals were washed with 40 ml of methylcyclohexane, thereafter dried at 65° C. to obtain 15.3 g of cis isomer of 98.3 wt % purity.

The yield of cis isomer from the isomer mixture was 92.8% and the trans isomer content in the crystals was 0.9 wt %. Melting point of recrystallized product was 115.6° C.

EXAMPLE 2 TO 5

Separation of cis isomer of 5-(4-chlorobenzyl)-2,2-dimethyl-1-(1H-1,2,4-triazol-1-ylmethyl)cyclopentanol 20.0 g of a mixture of 81.0 wt % of cis isomer and 19.0 wt % of trans isomer of 5-(4-chlorobenzyl)-2,2-dimethyl-1-(1H-1,2,4-triazol-1-ylmethyl)cyclopentanol was dissolved in 300 ml of toluene, and after addition of sulfuric acid in an amount shown in Table 1 at 20° C., heated to 100° C. on oil bath, causing a dehydration reaction. Thereafter, the reaction solution was treated as in Example 1.

TABLE 1

| Example | H$_2$SO$_4$ (%) | H$_2$SO$_4$/isomer mixture molar ratio | Reaction time (hours) | Cis/trans ratio (wt %) |
|---|---|---|---|---|
| 2 | 53 | 5.4/1.0 | 5.6 | 98.7/1.3 |
| 3 | 60 | 3.4/1.0 | 3.0 | 97.9/2.1 |
| 4 | 70 | 2.0/1.0 | 4.5 | 95.3/4.7 |
| 5 | 80 | 1.5/1.0 | 2.0 | 99.2/0.8 |

EXAMPLE 6

Separation of cis isomer of 5-(4-chlorobenzyl)-2,2-dimethyl-1-(1H-1,2,4-triazol-1-ylmethyl)cyclopentanol To 100 g of toluene solution containing cis isomer 12.1 g and trans isomer 3.1 g of 5-(4-chlorobenzyl)-2,2-dimethyl-1-(1H-1,2,4-triazol-1-ylmethyl)cyclopentanol, was added 1.39 g of 95% sulfuric acid (molar ratio of sulfuric acid to the total of cis isomer and trans isomer in 100 g of toluene solution=0.3/1.0) and heated at reflux, causing azeotropic dehydration with toluene.

After 5 hours, the reaction solution was cooled, and after addition of 50 g of 3% aqueous sodium hydroxide solution, stirred vigorously.

Then, the toluene layer, after washing 3 times with water, was dried over anhydrous sodium sulfate and toluene was distilled off under reduced pressure to obtain 23.27 g of residue.

The residue contained 51.4 wt % of cis isomer and 1.1 wt % of trans isomer. The yield of cis isomer at this stage from the toluene solution was 98.5% and the decomposition ratio of trans isomer was 91.8%.

The obtained residue was dissolved in 80 ml of methylcyclohexane at 75° C., and then cooled to 0° C. at a rate of 10° C./60 min. The precipitated crystals were filtered off, and the filtered crystals were washed with 35 ml of methylcyclohexane, thereafter dried at 65° C. to obtain 11.64 g of crystals.

Purity of cis isomer: 97 wt %;

Overall yield of cis isomer from the toluene solution: 93.0%;

Trans isomer content in the crystals: 0.9 wt %.

EXAMPLE 7

Separation of cis-cis isomer of 2-(4-chlorobenzyl)-5-isopropyl-1-(1H-1,2,4-triazol-1-ylmethyl)cyclopentanol 70 g of a mixture of 2-(4-chlorobenzyl)-5-isopropyl-1-(1H-1,2,4-triazol-1-ylmethyl) cyclopentanol isomers having a composition each shown in table 2, was dissolved in 500 ml of toluene, and after addition of 10 g of 95% sulfuric acid, heated at reflux, causing azeotropic dehydration with toluene.

After 4 hours, the reaction solution was cooled, and addition of 600 ml of 3% aqueous sodium hydroxide solution, stirred vigorously.

Then, the toluene layer, after washing 3 times with water, was dried over anhydrous sodium sulfate and toluene was distilled off under reduced pressure to obtain 68 g of residue.

The residue contained 70.7 wt % of cis-cis isomer and the yield thereof at this stage was 98.1%.

The obtained residue was recrystallized from a mixed solvent of 70 ml of n-hexane and 7 ml of ethyl acetate to obtain 45.7 g of crystals.

Purity of cis-cis isomer: 97.2 wt %;
Overall yield: 90.6%.

TABLE 2

| | Isomer composition (wt %) | | | |
| --- | --- | --- | --- | --- |
| | cis-cis | cis-trans | trans-cis | trans-trans |
| Before dehydration | 70.0 | 8.1 | 18.2 | 3.2 |
| After dehydration | 70.7 | 0.4 | 0.9 | 0 |

In Table 2, sum of isomer composition (wt %) does not represent 100% and the remaining is composed of other ingredients. After the dehydration reaction, almost all remaining is composed of dehydrated products.

In "cis-cis", "cis-trans", "trans-cis" and "trans-trans", cis and trans preceding "-" indicate the configurational relationship of hydroxy group and benzyl group, and cis and trans following "-" indicate the configurational relationship of hydroxy group and isopropyl group.

EXAMPLE 8

Separation of cis isomer of 5-(4-chlorobenzyl)-2,2-dimethyl-1-(1H-1,2,4-triazol-1-ylmethyl)cyclopentanol using a strongly acidic cation exchange resin having a sulfo group as acid catalyst 20.0 g of a mixture of 81.0 wt % of cis isomer and 19.0 wt % of trans isomer of 5-(4-chlorobenzyl)-2,2-dimethyl-1-(1H-1,2,4-triazol-1-yl)methylcyclopentanol was dissolved in 300 ml of toluene, and after addition of 10.0 g of a strongly acidic cation exchange resin having a sulfo group, "Amberliste 15" (available from Rohm & Haas Corp.), heated at reflux on oil bath, causing azeotropic dehydration with toluene.

After 5 hours, the reaction solution was cooled to 60° C., and after addition of 100 ml of ethanol containing 5 g of sodium hydroxide, stirred vigorously. Thereafter, the strongly acidic cation exchange resin was filtered off. The obtained filtrate, after washing 3 times with 400 ml of water, was dried over anhydrous sodium sulphate.

After dried, toluene was distilled off under reduced pressure to obtain 19.5 g of solid.

The solid contained 80.8 wt % of cis isomer and 1.3 wt % of trans isomer. The yield of cis isomer at this stage was 97.3% and the decomposition ratio of trans isomer was 93.4%.

The solid obtained after the dehydration was dissolved in 160 ml of methylcyclohexane with heating, and then cooled to 0° C. at a rate of 10° C./60 min. The precipitated crystals were filtered off, and the filtered crystals were washed with 40 ml of methylcyclohexane, thereafter dried at 65° C. to obtain 15.6 g of crystals of 98.1% pure. The yield of cis isomer from the isomer mixture was 94.4% and the trans isomer content in the crystals was 0.9 wt %. Melting point of recrystallized product was 115.5° C.

COMPARATIVE EXAMPLE 1

Separation of cis isomer of 5-(4-chlorobenzyl)-2,2-dimethyl-1-(1H-1,2,4-triazol-1-ylmethyl)cyclopentanol according to recrystallization 20.0 g of a mixture of 81.0 wt % of cis isomer and 19.0 wt % of trans isomer of 5-(4-chlorobenzyl)-2,2-dimethyl-1-(1H-1,2,4-triazol-1-ylmethyl)cyclopentanol was dissolved in 150 ml of methylcyclohexane with heating and cooled to 0° C. at a rate of 10° C./60 min.

The precipitated crystals were filtered off, and the filtered crystals, after washing with 40 ml of methylcyclohexane, were dried at 65° C. to obtain 18.0 g of crystals.

The crystals contained 80.5 wt % of cis isomer and 15.0 wt % of trans isomer. The yield of cis isomer was 94.5%.

As described above, when a mixture of cis isomer and trans isomer was recrystallized directly without dehydration according to the present invention, the purity of cis isomer could not be increased.

COMPARATIVE EXAMPLE 2

Separation of cis isomer of 5-(4-chlorobenzyl)-2,2-dimethyl-1-(1H-1,2,4-triazol-1-ylmethyl)cyclopentanol according to recrystallization 20.0 g of a mixture of 81.0 wt % of cis isomer and 19.0 wt % of trans isomer of 5-(4-chlorobenzyl)-2,2-dimethyl-1-(1H-1,2,4-triazol-1-ylmethyl)cyclopentanol was dissolved in 900 ml of methylcyclohexane with heating and cooled to 0° C. at a rate of 10° C./60 min. The precipitated crystals were filtered off, and the filtered crystals, after washing with 40 ml of methylcyclohexane, were dried at 65° C. to obtain 11.4 g of crystal.

The crystals contained 91.5 wt % of cis isomer and 8.5 wt % of trans isomer. The yield of cis isomer was 64.3%.

As described above, when a mixture of cis isomer and trans isomer was recrystallized in large amount of solvent without dehydration according to the present invention, the purity of cis isomer could not be increased to 95 wt % or more and the yield extremely reduced.

What is claimed is:

1. A process for separating a cis isomer from a mixture of the cis isomer and a trans isomer of an azolylmethylcyclopentanol derivative of the formula (I): wherein, $R^1$ and $R^2$ each independently represent a hydrogen atom or an alkyl group; each X represents a halogen atom, an alkyl group, a haloalkyl group, a phenyl group, a cyano group or a nitro group; n is an integer of from 0 to 5; A represents a nitrogen atom or a CH group; and each X may be identical or different when n is an integer of from 2 to 5, comprising the steps of dehydrating selectively the trans isomer in the presence of an acid and isolating the cis isomer.

2. A process according to claim 1, wherein the acid is selected from the group consisting of an inorganic acid, an aromatic sulfonic acid, a strongly acidic cation exchange resin having a sulfo group and a mixture thereof.

3. A process according to claim 1, wherein the dehydration is conducted in a diluent selected from the group consisting of an aromatic hydrocarbon and an alcohol.

4. A process according to claim 1, wherein $R^1$ and $R^2$ each independently represent a hydrogen atom or a $C_1$–$C_5$ alkyl group; each X represents a fluorine atom, a chlorine atom, a bromine atom, a $C_1$–$C_4$ alkyl group, a $C_1$–$C_4$ haloalkyl group, a phenyl group, a cyano group or a nitro group; n is an integer of from 0 to 2.

* * * * *